United States Patent [19]

Luebke et al.

[11] Patent Number: 5,449,501
[45] Date of Patent: Sep. 12, 1995

[54] APPARATUS AND PROCESS FOR CATALYTIC DISTILLATION

[75] Inventors: Charles P. Luebke, Mount Prospect; Terry L. Marker, Warrenville; Gregory A. Funk, Carol Stream, all of Ill.

[73] Assignee: UOP, Des Plaines, Ill.

[21] Appl. No.: 219,325

[22] Filed: Mar. 29, 1994

[51] Int. Cl.$^6$ .............................................. B01J 8/04
[52] U.S. Cl. ...................................... 422/193; 422/191; 422/211; 422/213; 422/219
[58] Field of Search ............... 422/191, 193, 195, 171, 422/213, 169, 211, 219; 203/DIG. 6

[56] References Cited

U.S. PATENT DOCUMENTS

| | | | |
|---|---|---|---|
| 3,506,408 | 4/1970 | Kageyama et al. | 422/191 |
| 4,302,356 | 11/1981 | Smith, Jr. | 203/DIG. 6 X |
| 4,624,748 | 11/1986 | Haunschild | 203/29 |
| 4,731,229 | 3/1988 | Spevandio | 422/188 X |
| 5,013,407 | 5/1991 | Nocca et al. | 422/193 X |
| 5,073,236 | 12/1991 | Gelbein et al. | 422/193 X |
| 5,082,990 | 1/1992 | Hsieh et al. | 585/467 |
| 5,108,550 | 4/1992 | Pinaire et al. | 203/1 |
| 5,130,102 | 7/1992 | Jones, Jr. | 422/191 |
| 5,133,942 | 7/1992 | Jones | 422/191 |
| 5,275,790 | 1/1994 | Buchholz et al. | 422/217 |

Primary Examiner—Timothy M. McMahon
Attorney, Agent, or Firm—Thomas K. McBride; John F. Spears, Jr.

[57] ABSTRACT

Hydrocarbons are converted in a novel catalytic distillation zone comprising two or more cylindrical beds of dense loaded catalyst. Each catalyst bed is penetrated by a plurality of vertical vapor passageways which provide a means for vapor communication between fractionation sections located above and below the catalyst beds. The dense loading of the catalyst provides a low cost method of placing a large quantity of catalyst into the apparatus.

11 Claims, 1 Drawing Sheet

APPARATUS AND PROCESS FOR CATALYTIC DISTILLATION

BACKGROUND OF THE INVENTION

1. Field of the Invention

The invention relates to a vapor-liquid contacting apparatus useful as a reactor in hydrocarbon conversion reactions. The invention more specifically relates to an apparatus and process for performing reactions by catalytic distillation. The invention therefore relates to apparatus for performing a liquid phase chemical reaction in the presence of a vapor phase containing one or more of the reactants, with the overall apparatus also performing a simultaneous separation by fractional distillation of a resultant reaction product from the reactants.

2. Related Art

Catalytic distillation is an established commercial process used in the production of methyl tertiary butyl ether (MTBE) a high octane motor fuel blending component desired for its oxygen content and ability to help satisfy government mandated oxygen contents for gasoline.

U.S. Pat. No. 4,624,748 issued to W. M. Haunschild discloses a catalytic distillation column reactor in which the catalyst is retained in an annular bed surrounded by porous walls. The catalyst may be withdrawn and replaced by slurrying the catalyst and then transferring the slurry through the conduits provided at the top and bottom of the annular bed.

U.S. Pat. No. 5,082,990 issued to C. R. Hsieh illustrates a catalytic distillation column having alternating sections of catalyst and distillation packing. The apparatus is used for the alkylation of aromatic hydrocarbons.

U.S. Pat. No. 5,108,550 issued to R. Pinnaire et al. discloses a catalytic distillation column in which porous catalyst retention tubes extend downward through a plurality of fractionation trays. The catalyst may be moved downward through the tubes to allow replacement of the catalyst.

U.S. Pat. No. 5,130,102 issued to E. M. Jones, Jr. illustrates another device for catalytic distillation. In this device the catalyst may be retained upon a screen. Liquid flows downward through downcomers and then rises upward through a bed of catalyst and across a fractionation tray. Vapor passes upward through the bed of catalyst to the upper fractionation tray.

U.S. Pat. No. 5,133,942 issued to E. M. Jones illustrates yet another catalytic distillation apparatus. In this apparatus a screen retains catalyst upon the upper surface of a fractionation tray, with vapor rising through the tray keeping the catalyst in suspension such that it may be easily withdrawn from the overall apparatus.

U.S. Pat. No. 5,275,790 issued to M. Buchholz et al. illustrates an apparatus for catalytic distillation comprising a plurality of porous walled mass transfer devices which are surrounded by loose catalyst particles.

BRIEF SUMMARY OF THE INVENTION

The invention is a novel device for performing catalytic distillation. The device comprises one or more beds of dense loaded catalyst located at different elevations within a vertical vessel which also comprises fractionation trays or other vapor liquid media. The use of dense loaded catalyst eliminates the need for complicated and expensive reaction zone internals and allows facile replacement of the catalyst. Vapor passageways extend vertically through the catalyst beds to allow vapors to easily pass through the bed(s) of dense-loaded catalyst.

One broad embodiment of the invention may be characterized as an apparatus for performing catalytic distillation which comprises a cylindrical outer vessel having enclosed upper and lower ends; means for performing fractional distillation comprising an upper first and a lower second section of fractionation media, located at different levels in the outer vessel; a bed of dense-loaded catalyst located within the outer vessel at a level between said two first and second sections of fractionation media; and a plurality of substantially vertical vapor passageways extending vertically through the bed of dense-loaded catalyst, each passageway having porous sidewalls in contact with the dense loaded catalyst and providing a means for free vapor passage between the sections of fractionation media located immediately above and below the bed of dense loaded catalyst.

DETAILED DESCRIPTION AND PREFERRED EMBODIMENTS

Figure 1:
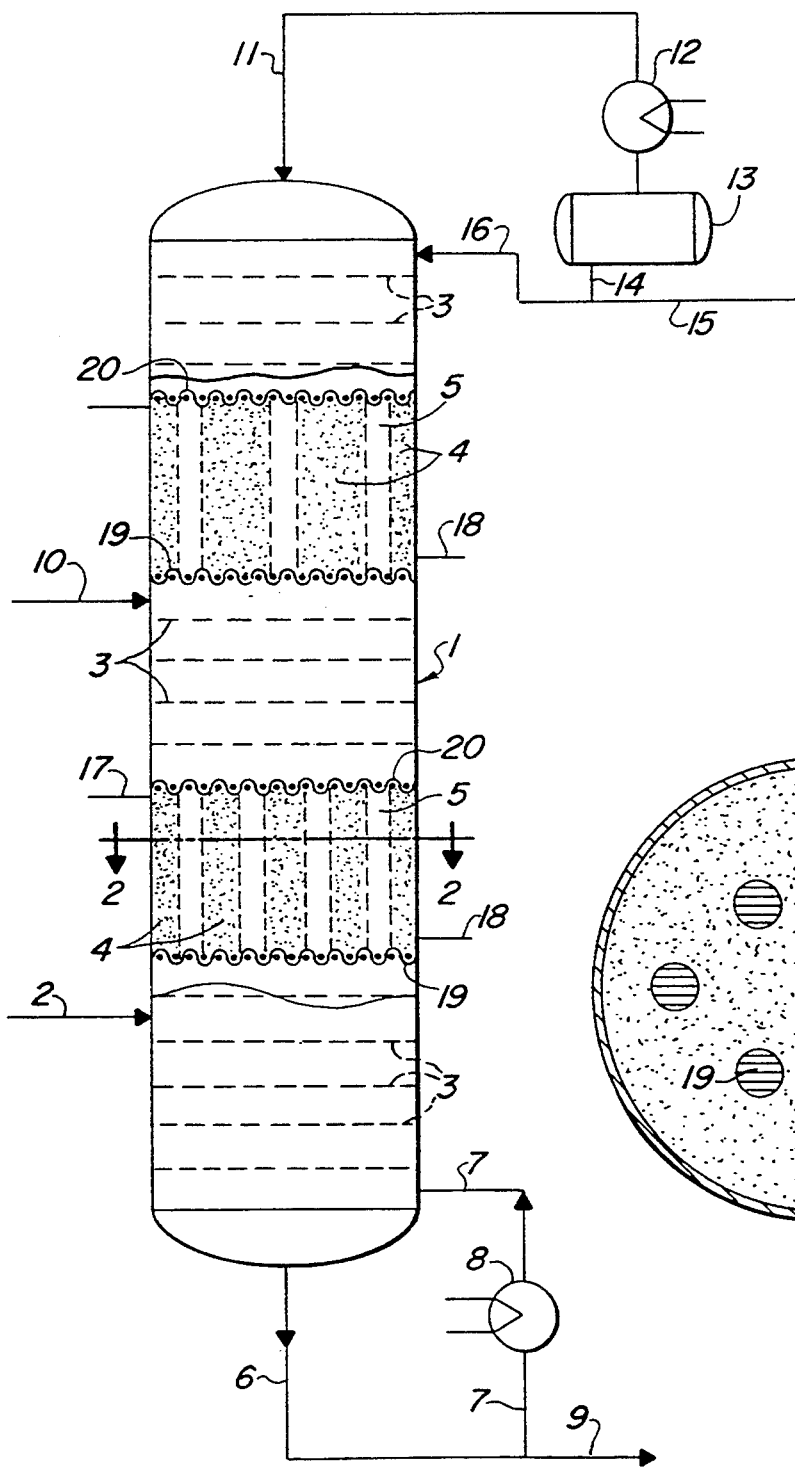
FIG. 1 is a partial sectional view of a catalytic distillation column 1 used for the production of ethers and having two separate dense loaded catalyst beds 4.

As previously stated, catalytic distillation is widely used in the petrochemical and refining industry for the production of ethers for use as motor fuel blending components. Catalytic distillation has also been proposed or is being used for a number of other reactions including the alkylation of $C_4$ paraffins for the production of motor fuel, the alkylation of aromatic hydrocarbons as for the production of cumene and the selective or total hydrogenation of olefinic hydrocarbons.

Catalytic distillation is employed to perform liquid-phase reactions which can be catalyzed by a solid catalyst at conditions which are also conducive to fractional distillation. It is therefore necessary to provide a means for the intimate contact of the liquid phase with the solid catalyst. It is also necessary to provide open space which allows vapor to pass through the overall apparatus in order to perform distillation. The result has been the development of a number of packing arrangements which retain the solid catalyst and provide a means to spread liquid over the catalyst surface while allowing gas to pass upward. Some of these materials are also effective in promoting the desired separation of product compounds and reactants by fractional distillation. That is, the catalyst retaining structure can be an effective structured packing for fractional distillation. One such structure is shown in U.S. Pat. No. 5,073,236.

The prior art arrangements for retaining the catalyst are very effective in providing good catalyst-liquid contact and in promoting the operation of the overall process, with some also providing good vapor liquid contacting for fractional distillation. However, any system which retains the catalyst in a prefabricated structure hinders replacement of the catalyst within the overall reactive-distillation vessel. Replacement of the catalyst in this instance will typically require that the vessel is removed from service and opened up to allow physical entry by service personnel, the removal of the catalyst retaining structure and its replacement. This may also require removal of some fractionation internals from the column to allow for this replacement. It is therefore an objective of this invention to provide a reactive distillation apparatus which allows facile replacement of the catalyst.

When the catalyst is retained within an overall structure intended to provide good vapor-liquid contact, this structure adversely impacts the cost of the reactive distillation zone as it inevitably costs more than dedicated vapor-liquid apparatus and is sometimes less effective for vapor-liquid contact. Finally, the open space in the catalyst retaining structure intended to allow for the passage of vapor detracts from the volume available for catalyst retention. As a result of this, catalyst-retaining devices which provide good vapor-liquid contacting tend to have a much lower catalyst density. When a large quantity of catalyst is required in the catalytic distillation zone, it is undesirable to have a low catalyst density as the required volume and cost of the catalytic distillation zone is increased by this low catalyst density. It is therefore another objective of the subject process to provide a catalytic distillation apparatus which employs dense loaded catalyst.

The subject invention achieves these objectives by the use of a unique apparatus that employs conventional fractional distillation equipment, such as trays or structured or dumped packing plus at least one and preferably two or more dense loaded catalyst beds having vapor passageways which allow the upward flow of vapor through the catalyst beds. The vapor rising from the distillation equipment is thereby allowed to bypass the catalyst bed resulting in a reduced pressure drop and a reduced tendency for the column to flood. In addition the use of a dense loaded bed of catalyst means that a much larger mass of catalyst can be located in the same volume of the vessel. The void volume in a packing arrangement such as described in U.S. Pat. Nos. 4,302,356 to L. A. Smith, Jr. and 5,073,236 to A. P. Gelbein can be as high as 80%. These two references are incorporated herein for their teaching as to the performance of catalytic distillation and the apparatus required to perform this process. In the subject process the void volume is much lower as the catalyst is present as a dense-loaded bed with noninherent void volume being introduced only by the vapor passageways. These passageways take up only a relatively small fraction of the cross-section of the column or the volume of the bed. By "dense loaded" it is meant that the catalyst is present as a uniform compact mass that is not separated or retained in position by mechanical spacers or other means. The catalyst is simply dumped into the available volume and left to settle to the form and density which conditions allow.

The performance of fractional distillation requires a large volume of vapor to rise upward through the column. In the subject invention the vertical vapor passageways allow the vapor to rise through the dense loaded catalyst bed without substantial effect on the catalyst bed. That is, most of the upward vapor flow is through the vapor passageways and therefore the catalyst is not disturbed. Some vapor flow is expected within the catalyst bed however due to the tendency of the liquid phase reactants in the catalyst bed to partially vaporize during the course of the exothermic reaction being performed in the zone. This vaporization serves as a means to remove heat from the site of the reaction and therefore acts as a very effective temperature control device. By controlling the pressure in the overall zone, it is possible to set the boiling point of the reactant mixture and thus set the reaction temperature.

In the subject process the nature of the dense loaded catalyst will inhibit vapor flow and thus the height of any one bed of dense loaded catalyst should not exceed approximately one meter. Vapor will flow horizontally if conditions allow and therefore will flow toward the vapor passageways which penetrate the dense loaded catalyst bed. This will ameliorate any fluidization problems which would otherwise occur due to liquid vaporization within the catalyst bed.

Catalytic distillation is primarily used to perform reactions which occur primarily in the liquid phase. It could be used to perform a vapor-phase reaction if mixed-phase conditions can be maintained in the system. The subject invention is not applicable to vapor-phase reactions. In the subject process and apparatus the liquid will be flowing downward through the dense bed. Assuming the feed point to the column is under the catalyst bed, the liquid will primarily result from condensation of vapor which has passed upward through the column via the vapor passageways. As the reaction proceeds the less volatile reaction product accumulates in the downward flowing liquid. When the liquid emerges from the catalyst bed and falls upon the fractionation means, the more volatile reactant compounds are concentrated in the rising vapor phase which travels upward through the column.

The subject invention can be best described by reference to the Drawing. FIG. 1 is a simplified flow diagram of catalytic distillation zone used to perform the etherification of isobutylene with methanol to form MTBE. This figure is not to scale and is intended only to illustrate the inventive concepts. The largest single piece of equipment in the apparatus is the column 1 having a vertical major axis and enclosed upper and lower ends. A heated liquid-phase feed stream comprising the isobutylene, typically in admixture with iso and normal butane and methanol enters the outer column 1 via line 2. This feed stream may contain MTBE produced in an upstream prereactor. The entering feed stream becomes admixed with the liquid phase material already present on the fractionation tray 3. The heat and vapors present at this point cause most of the C4-minus hydrocarbons and methanol present on this tray to enter the vapor phase and rise upward through the vessel. Since the majority of the cross-section of the vessel is occupied by the lower bed of dense loaded catalyst 4, most of the vapor passes into the vertical conduits 5 which function as vapor passageways. These passageways have a vertical axis aligned with the axis of column 1 and are formed from cylinders of porous screen or other material. They have a total cross-sectional area equal to about 1 to about 30 percent of the total internal cross-section of the outer vessel. The total cross-sectional area of the passageways should be such as to prevent an undue pressure drop across the catalyst bed. Each vapor passageway is preferably at least 3 centimeters in diameter and more preferably at least 5 centimeters in diameter.

As the vapors travel upward through the column, they come into contact with liquid resulting in transfer of some reactive isobutylene and methanol to the liquid phase. As there may be little vapor rising upward through the beds of densely packed catalyst, there will only be minimal mass transfer in these beds and the liquid may become depleted in one or both of these reactants. The vapor-liquid equilibrium is reestablished during contact between the two phases on the fractionation trays located above and below the catalyst beds. In addition at the top of the column the remaining vapors are withdrawn via line 11 and passed into the overhead condenser 12 in the manner of a normal fractionation column. This causes the formation of a liquid phase stream which is collected in the overhead receiver 13. The overhead liquid is withdrawn via line 14 and divided into a first portion which is returned to the vessel as reflux liquid via line 16 and a second portion which is removed as a net overhead stream via line 15. The net overhead stream serves as a means to remove nonreactive light hydrocarbons such as normal butane which enter the vessel in the feed stream.

The cooling effect provided by the incoming reflux liquid results in most of the rising isobutylene and methanol vapor passing into the liquid phase at least momentarily on the fractionation trays 3 located in the uppermost portion of the vessel. The liquid phase descends through the column and falls from the fractionation trays onto the screen covering the top of the upper bed of dense-loaded catalyst 4. The liquid enters the top of the dense loaded catalyst bed and flows downward through it. The upper bed can be constructed in the same manner as the lower bed or there may be differences in its construction to accommodate changes in vapor flow rates or desired reaction conditions. In the drawing this is represented by the upper bed having fewer vapor passageways 5 than the lower bed. A secondary feed line 10 is provided to allow the addition of methanol or isobutylene or both at an intermediate point just below the upper catalyst bed. This line is optional.

The Drawing also illustrates the provision of optional catalyst transfer lines 17 and 18 which allow respectively for the addition and withdrawal of catalyst from each of the catalyst beds. In the case of a resin type catalyst, it has been found very easy to transport the catalyst in the form of a slurry. A minimal amount of liquid is required to make a free flowing stream which can be pumped or allowed to flow by gravity to transfer catalyst. The liquid can be easily separated from entering catalyst by allowing it to drain downward through the screen 19 at the bottom of the bed. As the slurry will basically follow the liquid flow, if the liquid velocity is sufficient, there is considerable flexibility in the location of the feed and withdrawal points.

The catalyst is retained in the catalyst beds by an upper screen 20 and a lower screen 19. Preferably these are circular screens having a shape corresponding to the interior of the outer vessel 1. It is preferred that the screens do not cover the openings at the upper and lower ends of the vapor passageways 5. The upper screen 20 primarily functions to retain catalyst during catalyst transfer operations and any upsets during operation of the apparatus. It is intended to prevent catalyst leaving the dense-loaded bed and then entering into the vapor passageways. The lower catalyst screen 19 must support the weight of the retained catalyst and the liquid on the catalyst. The lower screen must therefore be supported by structural elements not shown on the drawing.

The bottom of the apparatus functions in a manner similar to a conventional fractionation column. The trays 3 located in the bottom section of the column beneath the lower catalyst bed promote the separation of the relatively more volatile compounds into the vapor phase. The liquid exiting the column in line 6 is thereby depleted of volatile compounds and enriched in the product ether. A portion of this liquid is diverted through line 7 and the reboiler 8 to supply heat and vapors to the lower end of the column. The remainder of this liquid is withdrawn from the process in line 9 as the net product stream of the process.

Figure 2:
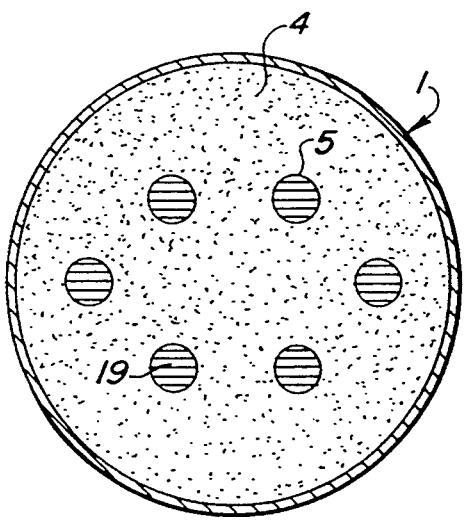
FIG. 2 is a cross-sectional view looking downward at the apparatus of FIG. 1 taken on a horizontal plane across the lower dense-loaded catalyst bed.

FIG. 2 illustrates the view seen looking downward at a horizontal cross-section of the column at a point in the lower catalyst bed. This view illustrates six vapor passageways 5 distributed through the dense bed of catalyst 4 to allow the vertical flow of vapor through the bed. In this view the lower catalyst retaining screen 19 is shown as covering the opening at the bottom of the passageways. This view also illustrates that the subject apparatus does not include a conduit or downcomer allocated for the downward flow of liquid to the next layer of fractionation media. That is, the wall of the outer vessel function and the lack of any downcomer functions as a means to confine the liquid flow to the catalyst bed.

The passageways should be uniformly distributed throughout the catalyst bed such that the horizontal gas flow is equal in all directions and channeling is avoided. There is no perceived requirement for the conduits forming the passageways to be absolutely straight or absolutely vertical. They may be inclined, curved or even somewhat twisted (e.g., coiled) in nature. As previously mentioned, the passageways preferably have porous walls which allow vapor to flow horizontally out of the beds into the passageways. This facilitates liquid vaporization for heat removal without fluidization of the bed. Alternatively, the passageways can be substantially imperforate. This embodiment fulfills the primary objective of allowing sufficient upward vapor flow to prevent "flooding" of the catalyst bed. If the walls of the passageways are porous, the openings must not allow catalyst particles to enter the passageway. A woven wire mesh over a perforated tube or well screen material as formed from closely-spaced windings are examples of suitable passageway materials. The passageways and the other vessel internals are preferably made from steel of a suitable nature to withstand the reactants. The passageways may also be made from a suitable plastic.

While the Drawing has been described in terms of the production of MTBE, it is not intended to limit the invention to this particular chemical reaction. Essentially identical procedures are followed in the production of other ethers which would result from the charging of different alcohols or isoolefins to the process. For instance, ethanol could be used instead of methanol or isoamylene could be consumed instead of isobutylene, with tertiary amyl methyl ether (TAME) being produced instead of MTBE.

A preferred embodiment of the subject invention can accordingly be characterized as a catalytic distillation reactor which comprises a cylindrical outer vessel having a cylindrical sidewall, an enclosed upper first end and an enclosed lower second end; a first fractionation section comprising a plurality of vapor-liquid contacting trays located in an upper portion of the vessel; a cylindrical bed of dense-loaded catalyst located below the first fractionation section and occupying substantially all of the cross-sectional area of the outer vessel; a second fractionation section comprising a plurality of vapor-liquid contacting trays located below the first bed of dense-loaded catalyst; and, a plurality of vapor passageways having porous sidewalls and extending vertically through the dense-loaded catalyst bed and being in open communication with the first and second fractionation sections.

It is believed the subject apparatus can be used to perform any reaction which is amendable to catalytic distillation. In general this includes any exothermic reaction which occurs primarily in the liquid phase and produces a reaction product which is less volatile than the feed compounds. It is also required that there exist a catalyst which promotes the desired reaction at conditions which are suitable for the separation of the reactants and product compound by fractional distillation. Nonlimiting examples of these reactions are etherification of iso olefins, alkylation of paraffins and aromatics including benzene and toluene, isomerization of olefins, reaction of mercaptans with olefins, the reaction of organic acids with alcohols to form esters, olefin hydration, olefin oxidation, etc.

An acidic resin catalyst is widely used for etherification. Resin catalysts are described in U.S. Pat. Nos. 3,784,399; 3,849,243; 4,751,343 and 5,012,031. The subject apparatus may contain a variety of other catalysts, with the catalyst composition being governed by its suitability for promoting the reaction under catalytic distillation conditions rather than any specific requirement imposed by the apparatus. Zeolitic catalysts such as those containing zeolite Y and zeolite beta are widely described as being useful in promoting alkylation and therefore can be used in the subject invention. The shape of the catalyst can be chosen as to maximize performance of the process, with the use of spherical, cylindrical or polylobial catalyst being foreseen. Furthermore the subject apparatus is subject to all of the variations that can be applied to catalytic distillation including the use of two or more different catalysts in the same or different beds and the use of different fractionation media.

The fractionation sections of the apparatus preferably contain fractionation trays. The exact type of tray is not believed to limit the practice of the invention and the apparatus may therefore employ sieve trays, dual flow trays, bubble cap trays, Multiple Downcomer trays, etc. The apparatus may employ two different types of trays or may employ structured or random packing instead of trays. As yet another alternative the subject apparatus may contain both packing and trays in the same or different fractionation sections.

Another basic variation of the subject invention is the distribution of the total catalyst into more than two dense-loaded catalyst beds. This can be done in several ways. For instance, the catalyst can be loaded into three or four separate dense-loaded beds. Some of the catalyst could alternatively be loaded into prior art catalytic distillation column packing devices (e.g., U.S. Pat. No. 5,073,236) located above, below or between the dense-loaded catalyst beds.

Operating conditions suitable for the reaction zone of the subject process during hydrocarbon conversion reactions such as etherification include a temperature of about 35 to about 100 degrees C, preferably 50 to 80 degrees C, and a pressure as required to maintain at least a portion (greater than 50 mole %) of the feed hydrocarbon present as a liquid. A general range of operating temperatures for hydrocarbon conversion is from about 0.5 to about 15 atmospheres.

What is claimed:

1. An apparatus for performing catalytic distillation which comprises:

(a) a cylindrical outer vessel having enclosed upper and lower ends;
(b) means for performing fractional distillation comprising an upper first and a lower second section of fractionation media, located at different levels in the outer vessel;
(c) a unitary bed of dense-loaded catalyst located within the outer vessel at a level between said two first and second sections of fractionation media; and,
(d) a plurality of substantially vertical vapor passageways extending vertically through the bed of dense-loaded catalyst, and providing a means for free vapor passage between the first and second sections of fractionation media.

2. An apparatus for performing catalytic distillation which comprises:

(a) a cylindrical outer vessel having enclosed upper and lower ends;
(b) means for performing fractional distillation comprising an upper first and a lower second section of fractionation media, located at different levels in the outer vessel;
(c) a unitary bed of dense-loaded catalyst located within the outer vessel at a level between said two first and second sections of fractionation media; and,
(d) a plurality of substantially vertical vapor passageways extending vertically through the bed of dense-loaded catalyst, each passageway having porous sidewalls in contact with the dense loaded catalyst and providing a means for free vapor passage between the sections of fractionation media located immediately above and below the bed of dense loaded catalyst.

3. The apparatus of claim 2 further characterized in that each of the vapor passageways has a cross-sectional area equal to at least one percent of the cross-sectional area of the outer vessel.

4. The apparatus of claim 2 further characterized in that the vapor passageways are substantially straight and are aligned with the major axis of the outer vessel.

5. The apparatus of claim 2 further comprising a second bed of dense-loaded catalyst located in the outer vessel below the lower second section of fractionation media, with a second plurality of vapor passageways extending vertically through the second bed of dense-loaded catalyst.

6. The apparatus of claim 2 further comprising means to withdraw and add catalyst to the bed of dense loaded catalyst.

7. The apparatus of claim 2 further characterized in that the bed of dense-loaded catalyst occupies substantially all of the available cross-sectional area of the outer vessel except for the area devoted to the vapor passageways.

8. The apparatus of claim 2 further characterized in that at least three vapor passageways extend through the bed of dense-loaded catalyst.

9. A catalytic distillation reactor which comprises:

(a) a cylindrical outer vessel having a cylindrical sidewall, an enclosed upper first end and an enclosed lower second end;
(b) a first fractionation section comprising a plurality of vapor-liquid contacting trays located in an upper portion of the vessel;
(c) a cylindrical bed of dense-loaded catalyst located below the first fractionation section and occupying substantially all of the cross-sectional area of the outer vessel;

(d) a second fractionation section comprising a plurality of vapor-liquid contacting trays located below the first bed of dense-loaded catalyst; and, (e) a plurality of vapor passageways having porous sidewalls and extending vertically through the dense-loaded catalyst bed and being in open communication with the first and second fractionation sections.

10. The reactor of claim 9 further comprising conduits extending through the sidewall of the outer vessel to add and withdraw catalyst from the first and second beds of dense loaded catalyst.

11. The reactor of claim 9 further characterized in that each of the vapor passageways has a cross-sectional area equal to at least one percent of the cross-sectional area of the outer vessel.

* * * * *